United States Patent [19]

Gupta

[11] Patent Number: 5,171,846

[45] Date of Patent: Dec. 15, 1992

[54] METHOD OF PREFERENTIAL LABELLING OF A PHYCOBILIPROTEIN WITH A SECOND DYE FOR USE IN A MULTIPLE COLOR ASSAY AND PRODUCT FOR SUCH USE

[75] Inventor: Ravinder K. Gupta, Pembroke Pines, Fla.

[73] Assignee: Coulter Corporation, Hialeah, Fla.

[21] Appl. No.: 526,387

[22] Filed: May 21, 1990

[51] Int. Cl.$^5$ .................... C07K 15/22; C07K 17/02; G01N 33/533

[52] U.S. Cl. .................................. 530/400; 530/370; 530/395; 530/403; 530/404; 530/405; 530/408; 530/409; 530/410; 436/501; 436/536; 436/546

[58] Field of Search ............... 530/403, 409, 410, 370, 530/400, 395, 404, 405, 408; 436/536, 546, 501

[56] References Cited

U.S. PATENT DOCUMENTS

| | | | |
|---|---|---|---|
| 4,520,110 | 5/1985 | Stryer et al. | 436/501 |
| 4,542,104 | 9/1985 | Stryer et al. | 436/536 |
| 4,666,862 | 5/1987 | Chan | 436/501 |
| 4,677,061 | 6/1987 | Rose et al. | 435/39 |
| 4,859,582 | 8/1989 | Stryer et al. | 435/5 |
| 4,987,086 | 1/1991 | Brosnan et al. | 436/501 |

OTHER PUBLICATIONS

Aubry et al. (1990) J. Immunol Methods 128:39–49.
Glazer et al. (1983) Biophys. J. 43:383–386.
Scopes R. K. *Protein Purification* 2nd ed. 1987 Springer-Verlag N.Y. etc. pp. 166,167,176–179,180,315.
Yon (1978) Int. J. Biochem. 9:373–379.
Gooding (1986) BioChromatography 1(i):34–40.
Glazer et al. (1984) TIBS 9:423–427.
Harding in *Handbook of Expt'l Immunol.* D. M. Weir ed. 4th ed. vol. 1, pp. 31.1–31.12 (1986).
MacColl and Guard-Frier in *Phycobiliproteins* C.R.C. Press (1987) pp. 1–7.
Product Bulletin on Streptavidin DuoChrome Becton Dickenson.
F. Haurowitz, "The Chemistry and Function of Proteins" (Academic Press, New York 1963), pp. 154–159.
A. L. Lehninger, "Biochemistry, 2nd Ed". (Worth Publisher, New York 1981) pp. 62–63, 39–44, 57, 125, 142–145.
R. K. Scopes, "Protein Purification, Practice and Principles", 2nd Ed. (Springer-Verlag, New York 1987), p. 30.
H. R. Mahler et al., "Biological Chemistry", 2nd Ed. (Harper & Row, New York 1971), pp. 99–100 and 106.
I. Rosengren et al., Biochem. Biophys. Acta, 412: 51–61 (1975).

*Primary Examiner*—Christine M. Nucker
*Assistant Examiner*—Kay K. Kim
*Attorney, Agent, or Firm*—Myron C. Cass

[57] ABSTRACT

A method for preparing a phycobiliprotein-Texas Red conjugate which overcomes the energy transfer/fluorescent quenching dilemma is disclosed. A phycobiliprotein, such as phycoerythrin, is conjugated with dye, such as Texas Red, in the presence of a selective salt which causes a hydrophobic intramolecular rearrangement of the phycobiliprotein thereby exposing more hydrophobic sites for binding to Texas Red. The conjugate is useful in multiple color fluorescence assays without requiring the use of multiple exciting sources.

10 Claims, No Drawings

METHOD OF PREFERENTIAL LABELLING OF A PHYCOBILIPROTEIN WITH A SECOND DYE FOR USE IN A MULTIPLE COLOR ASSAY AND PRODUCT FOR SUCH USE

FIELD OF THE INVENTION

This invention relates generally to electron donoracceptor conjugates suitable for use in multiple color assay methods, and particularly to a method of producing phycobiliprotein-dye conjugates suitable for such use.

BACKGROUND OF THE INVENTION

The technique of fluorescence was first introduced by Coons in 1941. He used a blue fluorescing anthracene compound coupled to pneumococcus antiserum to detect bacterial antigens in tissue section. Subsequent to this initial discovery, many fluorescing materials have been investigated, but only two, the fluorochromes fluorescein and rhodamine, are widely used, particularly in the form of fluorescein isothiocyanate (FITC) and tetramethylrhodamine isothiocyanate (TRITC) respectively. FITC covalently binds to proteins at alkaline pH through the epsilon amino residues of lysine and through terminal amino groups. It adsorption maximum is at 490-495 nm and it emits its characteristic green color at 517nm. TRITC likewise binds to proteins, has its absorption maximum at 541 nm and emits its characteristic red color at 572 nm.

Fluorescence is the emission of light of one wavelength (color) by a substance that is being irradiated by light of a different wavelength. The emitted light is always of lower energy, hence longer wavelength, then the incident light. In clinical use, the strength of the fluorescence is dependent on the efficiency with which the fluorochrome transforms incident light into emitted light, the amount of dye present in the specimen under observation and the intensity of the incident light. The dye known as Texas Red, (sulforhodamine 101 sulfonyl chloride or sulforhodamine 101 acid chloride) has previously been investigated for clinical use in conjugation with phycoerythrins, but major problems were encountered. These problems were low fluorescent efficiency, inadequate energy transfer from the phycoerythrin to Texas Red and the instability of the phycoerythrin-Texas Red conjugate. Phycoerythrin-Texas Red conjugates are desirable, however, because the overlap of their absorption and emission spectra have the potential to give a strong fluorescence signal.

Low fluorescent efficiency occurs whenever fluorescent chromophores are spatially adjacent to each other. It is usually called concentration quenching. See R. P. Hughland, "Excited States of Biopolymers", R. F. Steins, Ed., p 47 (Plenum Press, New York, 1983). However, high levels of labelling, resulting in chromophores being spatially adjacent to each other, are required in order to assure adequate energy (electron) transfer from the phycoerythrin to the acceptor dye chromophore. The net result is that the trade off required by the opposing effects results in less than optimal performance. Recently, A. N. Glazer et al. have covalently linked a phycoerythrin to an allophycocyanin to produce a highly fluorescent tandem conjugate with an energy transfer efficiency of 90%. See A. N. Glazer et al., T.I.B.S, 9:423 (1984); Biophysics J., 43,386–386 (1983); and U.S. Pat. No. 4,542,104 (See also U.S. Patent No. 4,520,110 to L. Stryer et al. describing the use of phycobiliproteins as fluorescent probes for the analysis and separation of molecules and cells). However, forming a conjugate from two naturally occurring pigments derived from algae is much different from conjugating a synthetic dye such as Texas Red. In fact, the procedures usually followed for conjugating reactive dyes to proteins does not work with phycoerythrin Texas Red. Using such procedures, one obtains a complex with a low energy transfer efficiency at low levels of labelling or fluorescence quenching at high levels of labelling.

Phycoerythrin-Texas Red conjugates are known and are commercially available. For example, the phycoerythrin-Texas Red conjugate known as DuoCHROME TM is available bound to streptavidin from Becton Dickinson Immunology Systems, Mountain View, California (Catalog No. 9026). The available conjugates, however, suffer from the fact that they do not have uniform phycoerythrin-Texas Red ratios throughout the individual conjugate members. There are present over-labelled and underlabelled species as well as species having the desired or optimum degree of labelling. Consequently, energy transfer/quenching problems can arise depending upon the distribution of labelled species within the entire sample.

This invention solves the energy transfer/quenching problem encountered in phycoerythrin-Texas Red conjugates by preferentially labelling sites close to the chromophore regions of a phycoerythrin with Texas Red and separating overlabelled and underlabelled conjugates from conjugates having the desired degree of labelling by exploiting the differences in hydrophobic character of conjugates having different degrees of labelling.

SUMMARY OF THE INVENTION

A method is provided for preparing a phycobiliprotein-reactive dye conjugate which overcomes the problems relating to the energy transfer/fluorescent quenching phenomenon encountered in such conjugates. A reactive dye, such as Texas Red, is reacted with a phycobiliprotein, such as phycoerythrin, in the presence of a salt especially selected to cause an intramolecular rearrangement of the phycobiliprotein structure whereby to expose a multiplicity of sites in its hydrophobic region with which said dye can bind to form the desired conjugate. The reaction is controlled as to the anion of the selected salt, permitted time of reaction and temperature. Conjugates having the preferred degree of phycoeythrin-Texas Red conjugation are separated from overlabelled and underlabelled conjugates by hydrophobic interaction chromatography.

DETAILED DESCRIPTION OF THE INVENTION

The first feature of this invention, preferential site labelling, makes it possible to obtain a satisfactory level of electron transfer from a phycoerythrin to Texas Red even at low levels of Texas Red conjugation by bringing the dye and the chromophore of the phycoerythrin into close proximity. This is accomplished by making use of the hydrophobic tetrapyrrole (bilin) chromophores that biliproteins are known to possess. See R. McColl and D. Guard-Frier, Phycobiliproteins, Chapter 1, C.R.C. Press (1987). Specifically, when certain anions commonly used in some "salting-out" processes are added to a phycobiliprotein containing buffer solution, they cause the phycobiliprotein to undergo an intramolecular structural rearrangement which "open-up" or "exposes" hydrophobic sites on the protein by reducing steric hindrance about the site. As a result of this hydrophobic intramolecular rearrangement, the sites close to chromophores can more readily react with a reactive dye, such as Texas Red, to form a conjugate. The common ions used in this process may be any of the common ions used in "salting-out" processes, such as phosphate, acetate, citrate, sulfate, tartrate and the like. The preferred anions are sulfate, phosphate and acetate. The most preferred anion is sulfate because it has little or no effect on the pH of the solution. Typically, when using one of the preferred anions such as sulfate in a phycoerythrin-Texas Red (PETR) conjugation reaction, it was found that an anion concentration in the range of about 1% to about 4% in the reaction solution resulted in a PETR conjugate having significantly improved energy transfer efficiency as compared to a PETR control conjugate prepared in the absence of a preferred anion.

The phycobiliprotein and the reactive dye are reacted together for a time in the range of 10 minutes, at a pH greater than 7 and at a temperature of about 4° C. prior to sampling to determine if an overall adequate phycobiliprotein-dye conjugation ratio has been reached. The determination is carried out by chromatographically desalting a sample of the reaction mixture and spectroscopically determining the $A_{565}/A_{595}$ value. If the value is in the range of 2.9 to 3.2, the reaction mixture is quenched and chromatographcally desalted.

The separation of overlabelled and underlabelled conjugate species from those having the desired degree of labelling was accomplished using hydrophobic interaction chromatography with an appropriate column medium like butyl toyopearl. The PETR conjugate produced by this method can be used in conjunction with an antibody to stain different types of cell. The cells so stained will be dependent upon the choice of antibody. The importance lies in the fact that the PETR conjugates provides for a third color in fluorescence analysis with the use of only a single excitation wavelength of 488 nm. Thus the expense of multiple excitation sources is eliminated.

PREFERRED EXAMPLE

In a typical reaction, a purified R-Phycoerythrin (PE) solution [3.0 g PE, 45.04 ml solution; PE concentration 66.6 mg/ml in 2 mM EDTA-PBS (PBS=Phosphate Buffered Saline)] was cooled in ice-bath and treated dropwise, with stirring, with an ice-cold solution of PBS containing 2 mM EDTA (29.25 ml) 20% $Na_2SO_4$ (pH 7.0, 6.0 ml) and 1 M Potassium Borate (pH 9.80, 30 ml). To the resulting mixture was added with vigorous stirring and at 4° C. a 25-fold molar excess of Texas red (20mg/ml in anhydrous Dimethyl Formamide). The reaction was monitored by drawing 10 μl samples periodically and desalting them on a 0.5-2 ml Sephedex G-50 column in PBS. The protein containing peak was collected and its A565/A595 value determined spectrophotometerically. If the A565/A595 values remain above 3.2, even after 30 mins or more of reaction time, a further aliquot of Texas red solution was added to the reaction mixture. When A565/A595 value fell below 3.2, preferably in the range of 2.9-3.2, reaction was quenched by addition of an one-hundred fold molar excess of glycine to the reaction mixture. The reaction mixture was next desalted on a Sephadex G-50 column in PBS, 2mM EDTA. The phycoerythrin-Texas red conjugate, in the protein peak, was then chromatographically factionated on a butyl 650 M chromatographic column by eluting with reverse gradient (3% to 0%) of Sodium Sulfate in 100 mM potassium phosphate solution containing 2 mM EDTA at pH 7.0 ±0.1. Chromatographic fractions having the desired emission characteristics (high energy transfer and high quantum efficiency) were pooled, concentrated, desalted and reconcentrated to give a purified phcoerythrin-Texas Red conjugate. The purified PETR conjugate was used as a marker in fluorescent immunoassays. The PETR marker conjugates to protein-like substance such as antibodies and streptavidin using methods known in the art.

We claim:

1. A method of producing a phycobiliprotein-dye conjugate wherein said dye is Texas Red comprising, reacting in a buffer solution of pH greater than 8 an excess of said dye with a phycobiliprotein in the presence of at least one selected salt which effects an intramolecular rearrangement of said phycobiliprotein to expose multiple sites reactive with said dye, desalting the reaction and removing excess dye, and separating the phycobiliprotein-dye conjugate by a chromatographic means.

2. The method in accordance with claim 1 wherein the phycobiliprotein is phycoerythrin.

3. The method in accordance with claim 1 wherein the salt is one whose anion is selected from the group consisting of phosphate, sulfate, acetate, citrate and tartrate ions.

4. A method of producing a phycobiliprotein-dye conjugate wherein said dye is Texas Red comprising, reacting in a buffer solution of pH greater than 8 an excess of said dye with a phycobiliprotein in the presence of a selected salt which effects an intramolecular rearrangement of said phycobiliprotein to expose multiple sites reactive with said dye, desalting the reaction and removing excess dye, and separating the phycobiliprotein-dye conjugate by hydrophobic interaction chromatography.

5. The method in accordance with claim 4 wherein said phycobiliprotein is phycoerythrin.

6. The method in accordance with claim 4 wherein said salt is a salt whose anion is selected from the group consisting of phosphate, acetate, sulfate, citrate, and tartrate.

7. A method of producing a phycoerythrin-Texas Red conjugate comprising reacting an excess of Texas Red with the phycoerythrin at a pH greater than 8 in the presence of about 1% to about 4% of at least one selected salt, monitoring the reaction between Texas Red and phycoerythrin by means of the reaction's adsorption spectrum at wavelengths of 565 and 595 nanometers, quenching the reaction mixture at such time as monitoring indicated that a ratio of $A_{565}/A_{595}$ reaches a value in the range of 2.9-3.5, removing excess Texas Red and separating the phycoerythrin-Texas Red conjugate by hydrophobic interaction chromatography.

8. A phycoerythrin-Texas Red conjugate prepared by the process of claim 7.

9. The conjugate prepared in accordance with to claim 1.

10. The conjugate prepared in accordance with claim 4.

* * * * *